United States Patent
Kim et al.

(10) Patent No.: US 9,751,981 B2
(45) Date of Patent: Sep. 5, 2017

(54) MANUFACTURING METHOD OF ORGANIC ZINC CATALYST AND MANUFACTURING METHOD OF POLYALKYLENE CARBONATE RESIN

(71) Applicant: LG CHEM, LTD., Seoul (KR)

(72) Inventors: Sung-Kyoung Kim, Daejeon (KR); Seung Young Park, Daejeon (KR); Hyun Ju Cho, Daejeon (KR)

(73) Assignee: LG Chem, Ltd., Seoul (KR)

(*) Notice: Subject to any disclaimer, the term of this patent is extended or adjusted under 35 U.S.C. 154(b) by 0 days.

(21) Appl. No.: 14/917,219

(22) PCT Filed: Oct. 30, 2014

(86) PCT No.: PCT/KR2014/010302
§ 371 (c)(1),
(2) Date: Mar. 7, 2016

(87) PCT Pub. No.: WO2015/065066
PCT Pub. Date: May 7, 2015

(65) Prior Publication Data
US 2016/0194442 A1   Jul. 7, 2016

(30) Foreign Application Priority Data

Oct. 30, 2013 (KR) .................. 10-2013-0129956
Oct. 29, 2014 (KR) .................. 10-2014-0148459

(51) Int. Cl.
*C08G 64/34* (2006.01)
*C07C 51/41* (2006.01)
(Continued)

(52) U.S. Cl.
CPC .............. *C08G 64/34* (2013.01); *B01J 31/12* (2013.01); *C07C 51/412* (2013.01); *C08K 5/0091* (2013.01)

(58) Field of Classification Search
CPC ...................................................... C08G 64/34
(Continued)

(56) References Cited

U.S. PATENT DOCUMENTS 4,783,445 A   11/1988 Sun
4,943,677 A   7/1990 Rokicki
(Continued)

FOREIGN PATENT DOCUMENTS

CN   1322220 A   11/2001
CN   1692135 A   11/2005
(Continued)

OTHER PUBLICATIONS

Kim, Jong-Seong, et al., "Hydrothermal Synthesis of Single-Crystalline Zinc Glutarate and Its Structural Determination," Chem. Mater. 2004, vol. 16, No. 16, 2004, pp. 2981-2983.
(Continued)

*Primary Examiner* — Duc Truong
(74) *Attorney, Agent, or Firm* — Dentons US LLP

(57) ABSTRACT

The present invention relates to a manufacturing method of an organic zinc catalyst having more uniform and finer particle size and showing a more improved activity in a polymerization process for manufacturing a polyalkylene carbonate resin, and a manufacturing method of the polyalkylene carbonate resin using the organic zinc catalyst obtained by the manufacturing method of the organic zinc catalyst, the manufacturing method of an organic zinc catalyst including: forming a zinc dicarboxylate-based catalyst by reacting a zinc precursor with C3-C20 dicarboxylic acid, wherein the reaction step is performed under a condition in which the number of moles of the dicarboxylic acid is more than that of the zinc precursor in a reaction system, throughout the entire reaction step.

12 Claims, 2 Drawing Sheets

(51) Int. Cl.
*B01J 31/12* (2006.01)
*C08K 5/00* (2006.01)

(58) Field of Classification Search
USPC .......................................................... 528/414
See application file for complete search history.

(56) References Cited

U.S. PATENT DOCUMENTS

| | | |
|---|---|---|
| 4,960,862 A | 10/1990 | Carroll et al. |
| 4,981,948 A | 1/1991 | Kawachi et al. |
| 5,026,676 A | 6/1991 | Motika et al. |
| 5,811,365 A | 9/1998 | Barry |
| 5,945,458 A | 8/1999 | Barry |
| 7,405,265 B2 | 7/2008 | Moon et al. |
| 8,507,708 B2 | 8/2013 | Dehghani et al. |
| 2003/0134740 A1 | 7/2003 | Meng et al. |
| 2004/0214718 A1 | 10/2004 | Meng et al. |
| 2005/0272904 A1 | 12/2005 | Moon et al. |
| 2009/0240025 A1 | 9/2009 | Fujimoto et al. |
| 2011/0152377 A1 | 6/2011 | Hanma et al. |

FOREIGN PATENT DOCUMENTS

| | | | |
|---|---|---|---|
| CN | 102166516 A | | 8/2011 |
| CN | 102439062 A | | 5/2012 |
| CN | 102872919 A | | 1/2013 |
| EP | EP0358326 | * | 12/1996 |
| EP | 2433976 A1 | | 3/2012 |
| JP | 02-292328 A | | 12/1990 |
| JP | 08-504163 A | | 5/1996 |
| JP | 2732475 B2 | | 3/1998 |
| JP | 3000064 B2 | | 1/2000 |
| JP | 2005-530021 A | | 10/2005 |
| JP | 2005-530022 A | | 10/2005 |
| JP | 2006002063 A | | 1/2006 |
| JP | 2006-503946 A | | 2/2006 |
| JP | 2007-126547 A | | 5/2007 |
| JP | 2010-287563 A | | 12/2010 |
| JP | 2012-180445 A | | 9/2012 |
| JP | 2012-232287 A | | 11/2012 |
| JP | 2013-212973 A | | 10/2013 |
| KR | 10-1993-0003163 B1 | | 4/1993 |
| KR | 10-1998-0020821 A | | 6/1998 |
| KR | 10-1998-0034110 A | | 8/1998 |
| KR | 10-2003-0097236 A | | 12/2003 |
| KR | 10-2003-0097237 A | | 12/2003 |
| KR | WO 2004/000912 | * | 12/2003 |
| KR | 10-0722380 B1 | | 5/2007 |
| KR | 10-2009-0025219 A | | 3/2009 |
| KR | 10-2012-0023820 A | | 3/2012 |
| KR | 10-2013-0044223 A | | 5/2013 |
| WO | 00-14141 A1 | | 3/2000 |
| WO | 2010-016219 A1 | | 2/2010 |
| WO | 2010/069000 A1 | | 6/2010 |
| WO | 2011-004730 A1 | | 1/2011 |
| WO | 2011-107577 A2 | | 9/2011 |

OTHER PUBLICATIONS

Kim, Jong-Seong, et al., "Synthesis of Zinc Glutarates with Various Morphologies Using an Amphiphilic Template and Their Catalytic Activities in the Copolymerization of Carbon Dioxide and Propylene Oxide," Wiley InterScience, 2005, pp. 4079-4088. http://www.nihs.go.jp/ICSC/icssj-c/icss0806c.html (http://www.inchem.org/documents/icsc/icsc/eics0806.htm).

* cited by examiner

MANUFACTURING METHOD OF ORGANIC ZINC CATALYST AND MANUFACTURING METHOD OF POLYALKYLENE CARBONATE RESIN

This application is a National Stage Entry of International Application No. PCT/KR2014/010302, filed Oct. 30, 2014, and claims the benefit of Korean Application No. 10-2013-0129956, filed on Oct. 30, 2013, and Korean Application No. 10-2014-0148459, filed Oct. 29, 2014, all of which are hereby incorporated by reference in their entirety for all purposes as if fully set forth herein.

BACKGROUND OF THE INVENTION (a) Field of the Invention

The present invention relates to a manufacturing method of an organic zinc catalyst having more uniform and finer particle size and showing a more improved activity in a polymerization process for manufacturing a polyalkylene carbonate resin, and a manufacturing method of the polyalkylene carbonate resin using the organic zinc catalyst obtained by the manufacturing method of the organic zinc catalyst.

(b) Description of the Related Art

Since the industrial revolution, modern society has been built by consuming a large amount of fossil fuels, but on the other hand, carbon dioxide concentration in the atmosphere has increased, and further, this increase has been more accelerated by environmental destruction such as disforestation, etc. Global warming is caused by an increase of greenhouse gases such as carbon dioxide, freon, and methane in the atmosphere, such that it is significantly important to reduce the atmospheric concentration of carbon dioxide highly contributing to global warming, and several studies into emission regulation, immobilization, etc., have been conducted on a global scale.

Among the studies, a copolymerization of carbon dioxide and epoxide developed by Inoue, et al., is expected as a reaction for solving the problems of global warming, and has been actively researched in view of immobilization of chemical carbon dioxide and in view of the use of carbon dioxide as a carbon resource. Particularly, a polyalkylene carbonate resin obtained by the polymerization of carbon dioxide and epoxide has recently received significant attention as a kind of biodegradable resins.

Various catalysts for manufacturing the polyalkylene carbonate resin have been researched and suggested for a long time, and as representative examples thereof, zinc dicarboxylate-based catalysts such as a zinc glutarate catalyst, etc., in which zinc and dicarboxylic acid are combined to each other have been known.

Meanwhile, the zinc dicarboxylate-based catalyst, as a representative example, a zinc glutarate catalyst is formed by reacting a zinc precursor with a dicarboxylic acid such as a glutaric acid, etc., and has a shape of fine crystalline particle. The zinc dicarboxylate-based catalyst having the crystalline particle shape has a difficulty in being controlled to have a uniform and fine particle size in a manufacturing process thereof. For reference, when it is possible to control the catalyst particle size to be finer, surface area is more increased and active sites of a catalyst surface are more increased in the same amount of catalyst, which is preferred. However, it is difficult to control the catalyst particle size to be fine and uniform.

Due to the above-described reasons, the existing known zinc dicarboxylate-based catalysts have a relatively large particle size and a non-uniform particle shape in many cases, and accordingly, when a polymerization process for manufacturing the polyalkylene carbonate resin is performed by using the zinc dicarboxylate-based catalyst, a sufficient contact area between reaction materials and the catalyst is not secured, such that there is a drawback in that a polymerization activity is not sufficiently implemented. Further, there are many cases in which an activity of the existing zinc dicarboxylate-based catalyst itself is not sufficient, either.

Further, the zinc dicarboxylate-based catalyst has difficulty in dispersing and controlling the catalyst particles in a reaction solution due to non-uniformity of the particle size.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a manufacturing method of an organic zinc catalyst having more uniform and finer particle size and showing a more improved activity in a polymerization process for manufacturing a polyalkylene carbonate resin, and an organic zinc catalyst obtained by the manufacturing method of the organic zinc catalyst.

In addition, the present invention has been made in an effort to provide a manufacturing method of the polyalkylene carbonate resin using the organic zinc catalyst obtained by the manufacturing method.

An exemplary embodiment of the present invention provides a manufacturing method of an organic zinc catalyst including: forming a zinc dicarboxylate-based catalyst by reacting a zinc precursor with C3-C20 dicarboxylic acid, wherein the reaction step is performed under a condition in which the number of moles of the dicarboxylic acid is more than that of the zinc precursor in a reaction system, throughout the entire reaction steps.

Another embodiment of the present invention provides an organic zinc catalyst in a particle shape having an average particle size of 0.8 μm or less and a particle size standard deviation of 0.2 μm or less, wherein the organic zinc catalyst is a zinc dicarboxylate-based catalyst obtained by reacting a zinc precursor with C3-C20 dicarboxylic acid.

Yet another embodiment of the present invention provides a manufacturing method of a polyalkylene carbonate resin including: polymerizing an epoxide and a monomer including carbon dioxide in the presence of the organic zinc catalyst as described above.

Hereinafter, the manufacturing method of the organic zinc catalyst according to exemplary embodiments of the present invention, the organic zinc catalyst obtained by the same, and the manufacturing method of the polyalkylene carbonate resin using the organic zinc catalyst are described in detail.

According to an exemplary embodiment of the present invention, there is provided a manufacturing method of an organic zinc catalyst including: forming a zinc dicarboxylate-based catalyst by reacting a zinc precursor with C3-C20 dicarboxylic acid, wherein the reaction step is performed under a condition in which the number of moles of the dicarboxylic acid is more than that of the zinc precursor in a reaction system, throughout the entire reaction steps.

Here, "a condition in which the number of moles of the dicarboxylic acid is more than that of the zinc precursor in a reaction system, throughout the entire reaction steps" means that a condition in which the number of moles of the dicarboxylic acid is always more than that of the zinc precursor in the reaction system (e.g., in a reactor) where a reaction thereof is performed, is maintained from a starting time for a reaction of the zinc precursor and the dicarboxylic acid up to an ending time for the reaction thereof, regardless of a total used amount (the number of moles) of the zinc precursor and the dicarboxylic acid required for manufacturing the organic zinc catalyst. As described below in more detail, in order to maintain the condition, the total used amount of the dicarboxylic acid may be added at the reaction time, or in the case of the zinc precursor, the total required amount may be separately added several times.

Meanwhile, as results from continuous experiments, the present inventors surprisingly confirmed that in the process of manufacturing the zinc dicarboxylate-based catalyst by reacting the zinc precursor with the dicarboxylic acid, when the reaction is performed in a state controlled so that the dicarboxylic acid is present in an excess amount (a molar excess amount) as compared to the zinc precursor during the entire reaction processes, the zinc dicarboxylate-based catalyst having a finer and more uniform particle size and showing a more improved activity than that of the existing catalysts could be manufactured.

It is considered that the reason is because when the reaction step is performed in a state in which the dicarboxylic acid is present in an excess amount (hereinafter, referred to as a molar excess state of the dicarboxylic acid), the reaction is slowly performed in a state in which respective zinc or precursor molecules or ions thereof are surrounded by dicarboxylic acid molecules or ions having excess amounts in the reaction system, such that the zinc or the precursor components thereof which are the catalytically active components hardly agglomerate with each other, and all react with the dicarboxylic acid components, thereby forming active sites of the catalyst.

Further, due to the reaction as performed above, it is thought that a possibility in which the respective zinc dicarboxylate-based catalyst particles agglomerate with each other in the manufacturing method thereof is decreased, thereby finally forming finer and more uniform catalyst particles. In addition, due to the reaction as performed above, it is expected to form the zinc dicarboxylate-based catalyst particles showing different crystalline characteristics from those of the existing catalyst particles.

To this end, according to an exemplary embodiment of the present invention, it was consequently confirmed that the zinc dicarboxylate-based organic zinc catalyst showing a more excellent activity could be obtained in the catalyst particle shape having the finer and more uniform particle size. In addition, due to the finer and uniform particle size of the catalyst particles, dispersing and controlling the catalyst particles in the reaction solution may be easily performed. Accordingly, the organic zinc catalyst may be preferably applied to the manufacturing of the polyalkylene carbonate resin by the reaction of carbon dioxide with epoxide.

On the other hand, it was confirmed that even though the total used amount of the dicarboxylic acid for manufacturing the organic zinc catalyst is larger than that of the zinc precursor, when the above-described condition, that is, the condition in which the dicarboxylic acid is present in the molar excess amount throughout the entire reaction steps, is not satisfied (for example, a case in which the dicarboxylic acid is slowly added and reacted with the zinc precursor such as Comparative Example to be described below, etc.,—since only a portion of the dicarboxylic acid is added to the reaction system at least at the reaction time, the molar excess amount of the dicarboxylic acid may not be maintained), the organic zinc catalyst having an agglomerated particle size as compared to the organic zinc catalyst obtained by the exemplary embodiment may be merely manufactured, which had a relatively poor activity.

Meanwhile, in the manufacturing method of the exemplary embodiment, several ways may be applied so that the condition in the reaction system is maintained as the state in which the dicarboxylic acid is present in the molar excess amount, throughout the entire reaction steps.

First, as a first way, the dicarboxylic acid may be used in a sufficient molar excess amount relative to the total used amount as compared to the zinc precursor, and in addition, the above-described molar excess amount condition of the dicarboxylic acid may be maintained throughout the entire reaction steps by adding the total used amount of the dicarboxylic acid at the reaction time. More specifically, the dicarboxylic acid may be used at a molar ratio of about 1.05 to 1.5, or about 1.1 to 1.3 relative to 1 mol of the zinc precursor, and in addition, the total used amount of the dicarboxylic acid may be added at the reaction time. By controlling the total used amount as described above, the reaction step is performed while maintaining the molar excess state of the dicarboxylic acid, thereby manufacturing the organic zinc catalyst in the zinc dicarboxylate-based catalyst shape having a more uniform and finer particle size and showing an improved activity.

Further, as a second way, the reaction step is performed in a liquid medium in which reaction materials including the zinc precursor and the dicarboxylic acid are present (for example, in a solution or a dispersion liquid in which the reaction materials are dissolved or dispersed), wherein the reaction step may be performed by separately adding the solution or the dispersion liquid containing the zinc precursor to the solution or the dispersion liquid containing the dicarboxylic acid two or more times. That is, some amount of the solution or the dispersion liquid containing the zinc precursor may be firstly added to perform the reaction, and then the remaining amount of the solution or the dispersion liquid containing the zinc precursor may be separately added later to perform the remaining reaction, such that the entire reaction steps may be performed while maintaining the molar excess state of the dicarboxylic acid in the reaction system, thereby manufacturing the organic zinc catalyst in the zinc dicarboxylate-based catalyst shape having a more uniform and finer particle size and showing an improved activity.

Here, the step of separately adding the solution or the dispersion liquid containing the zinc precursor two or more times is not particularly limited, and may be performed by several methods.

First, in an example, the total used amount of the zinc precursor may be separated into two to ten parts, and each of the obtained solutions or the obtained dispersion liquids containing the zinc precursor may be added to the solution or the dispersion liquid containing the dicarboxylic acid two to ten times at an equal time interval during the reaction. Here, preferably, each of the solutions or the dispersion liquids may be obtained by separating the total used amount of the zinc precursor into two to five parts, and may be separately added two to five times. Accordingly, it is possible to manufacture the organic zinc catalyst showing a more improved activity, etc., by effectively maintaining the molar excess condition of the dicarboxylic acid in the reaction system while more increasing productivity of the catalyst manufacturing process.

In another example, the entire reaction step may be performed by uniformly dropping the solutions or the dispersion liquids containing the zinc precursor in droplet forms onto the solution or the dispersion liquid containing the dicarboxylic acid.

Meanwhile, by applying the above-described first method (controlling of the total used amount) and the above-described second method (separate addition of the zinc precursor) together, the condition in which the molar excess condition of the dicarboxylic acid is always maintained throughout the entire reaction steps may be more appropriately achieved.

Meanwhile, in the manufacturing method of the organic zinc catalyst according to the exemplary embodiment as described above, the zinc precursor may be any zinc precursor used for manufacturing zinc dicarboxylate-based catalysts in the art without particular limitation. Specific examples of the zinc precursor may include zinc oxide, zinc sulfate ($ZnSO_4$), zinc chlorate ($Zn(ClO_3)_2$), zinc nitrate ($Zn(NO_3)_2$), zinc acetate ($Zn(OAc)_2$, zinc hydroxide, etc.

Further, as the dicarboxylic acid reacting with the zinc precursor, any C3-C20 dicarboxylic acid may be used. More specifically, an aliphatic dicarboxylic acid selected from the group consisting of a malonic acid, a glutaric acid, a succinic acid, and an adipic acid, or an aromatic dicarboxylic acid selected from the group consisting of a terephthalic acid, an isophthalic acid, a homophthalic acid, and a phenylglutaric acid may be used, and various C3-C20 aliphatic or aromatic dicarboxylic acids may be used in addition thereto. However, in view of an activity, etc., of the organic zinc catalyst, the dicarboxylic acid is preferably the glutaric acid and the zinc dicarboxylate-based organic zinc catalyst is preferably the zinc glutarate-based catalyst.

In addition, when the reaction step of the zinc precursor and the dicarboxylic acid is performed in a liquid medium, any organic or aqueous solvent that is known to be capable of uniformly dissolving or dispersing the zinc precursor and/or the dicarboxylic acid may be used as the liquid medium. Specific examples of the organic solvents may include at least one solvent selected from the group consisting of toluene, hexane, DMF, ethanol and water.

In addition, the reaction step of the zinc precursor and the dicarboxylic acid may be performed at a temperature of about 50 to 130° C. for about 1 to 10 hours. In addition, as previously described, the zinc precursor is separately added at the equal time interval in the total reaction time, such that the molar excess state of the dicarboxylic acid in the reaction system may be maintained throughout the entire reaction steps. By performing the reaction step under the reaction condition, the zinc dicarboxylate-based organic zinc catalyst having more uniform and finer particle size and showing improved physical properties may be manufactured at a high yield.

The manufacturing method of the organic zinc catalyst obtained by the above-described method is optimized as described above, such that the catalyst may be manufactured in a uniform particle shape having an average particle size of about 0.8 μm or less, or about 0.5 to 0.7 μm, and a particle size standard deviation of about 0.2 μm or less, about 0.1 μm or less, or about 0.05 to 0.1 μm, as compared to the existing catalyst manufactured by the existing method and having a particle size of about 1 to 2 μm. As described above, the organic zinc catalyst has more uniform and finer particle size, such that the organic zinc catalyst may have an increased surface area of about 1.8 $m^2/g$ or more, or about 1.8 to 2.5 $m^2/g$ as compared to the existing catalyst having a surface area of about 1.1 to 1.3 $m^2/g$. Accordingly, when the organic zinc catalyst is used as the catalyst at the time of manufacturing the polyalkylene carbonate resin by a copolymerization of carbon dioxide and epoxide, contact areas of catalyst particles and reaction materials may be more increased, thereby showing an improved activity.

Meanwhile, according to another exemplary embodiment of the present invention, there is provided a manufacturing method of a polyalkylene carbonate resin including: polymerizing an epoxide and a monomer including carbon dioxide in the presence of the organic zinc catalyst manufactured by the method of the above-described exemplary embodiment.

In the manufacturing method of the resin, the organic zinc catalyst may be used in a non-uniform catalyst form, and the polymerizing step may be performed in an organic solvent by solution polymerization. Accordingly, a heat of reaction may be appropriately controlled, and a molecular weight or a viscosity of the polyalkylene carbonate resin to be preferably obtained may be easily controlled.

In the solution polymerization, as the solvent, at least one selected from the group consisting of methylene chloride, ethylene dichloride, trichloroethane, tetrachloroethane, chloroform, acetonitrile, propionitrile, dimethylformamide, N-methyl-2-pyrrolidone, dimethyl sulfoxide, nitromethane, 1,4-dioxane, hexane, toluene, tetrahydrofuran, methyl ethyl ketone, methyl amine ketone, methyl isobutyl ketone, acetone, cyclohexanone, trichloroethylene, methyl acetate, vinyl acetate, ethyl acetate, propyl acetate, butyrolactone, caprolactone, nitropropane, benzene, styrene, xylene, and methyl propasol may be used. Among these examples of the solvent, when methylene chloride or ethylene dichloride is used as the solvent, the polymerization reaction may be more effectively performed.

The solvent may be used at a weight ratio of about 1:0.5 to 1:100 preferably, at a weight ratio of about 1:1 to 1:10 relative to the epoxide.

Here, when the ratio is less than about 1:0.5, which is excessively small, the solvent does not appropriately function as a reaction medium, such that it may be difficult to obtain the above-described advantages of the solution polymerization. Further, when the ratio is more than about 1:100, the concentration of epoxide, etc., is relatively decreased, such that productivity may be deteriorated, and a molecular weight of a finally formed resin may be decreased, or a side reaction may be increased.

Further, the organic zinc precursor may be added at a molar ratio of about 1:50 to 1:1000 relative to the epoxide. More preferably, the organic zinc precursor may be added at a molar ratio of about 1:70 to 1:600, or about 1:80 to 1:300 relative to the epoxide. When the molar ratio is excessively small, it is difficult to show a sufficient catalytic activity at the time of the solution polymerization. On the contrary, when the molar ratio is excessively large, since an excessive amount of the catalyst is used, the reaction is not efficiently performed, by-products may occur, or back-biting of the resin by heating in the presence of the catalyst may occur.

Meanwhile, as the epoxide, at least one selected from the group consisting of C2-C20 alkylene oxide unsubstituted or substituted with halogen or C1-C5 alkyl group; C4-C20 cycloalkylene oxide unsubstituted or substituted with halogen or C1-C5 alkyl group; and C8-C20 styrene oxide unsubstituted or substituted with halogen or C1-C5 alkyl group may be used. Representatively, as the epoxide, C2-C20 alkylene oxide unsubstituted or substituted with halogen or C1-C5 alkyl group may be used.

Specific examples of the epoxide include ethylene oxide, propylene oxide, butene oxide, pentene oxide, hexene oxide, octene oxide, decene oxide, dodecene oxide, tetradecene oxide, hexadecene oxide, octadecene oxide, butadiene monoxide, 1,2-epoxy-7-octene, epifluorohydrine, epichlorohydrine, epibromohydrine, isopropyl glycidyl ether, butyl glycidyl ether, t-butyl glycidyl ether, 2-ethylhexyl glycidyl ether, allyl glycidyl ether, cyclopentene oxide, cyclohexene oxide, cyclooctene oxide, cyclododecene oxide, alpha-pinene oxide, 2,3-epoxy norbornene, limonene oxide, dieldrin, 2,3-epoxypropylbenzene, styrene oxide, phenylpropylene oxide, stilbene oxide, chlorostilbene oxide, dichlorostilbene oxide, 1,2-epoxy-3-phenoxypropane, benzyloxymethyl oxirane, glycidyl-methylphenyl ether, chlorophenyl-2,3-epoxypropyl ether, epoxypropyl methoxyphenyl ether, biphenyl glycidyl ether, glycidyl naphthyl ether, and the like. As the most representative example, ethylene oxide is used as the epoxide.

In addition, the above-described solution polymerization may be performed at about 50 to 100° C. and about 15 to 50 bar for about 1 to 60 hours. Further, it is more preferable to perform the solution polymerization at about 70 to 90° C. and about 20 to 40 bar for about 3 to 40 hours.

Meanwhile, since the remaining polymerization process and condition except for the above description may follow general polymerization condition, etc., for manufacturing the polyalkylene carbonate resin, additional descriptions thereof will be omitted.

According to the present invention, the catalyst manufacturing process is optimized, such that the organic zinc catalyst for manufacturing the polyalkylene carbonate resin having a more uniform and finer particle size and showing an excellent activity may be manufactured and provided.

DETAILED DESCRIPTION OF THE EMBODIMENTS

Figure 1:
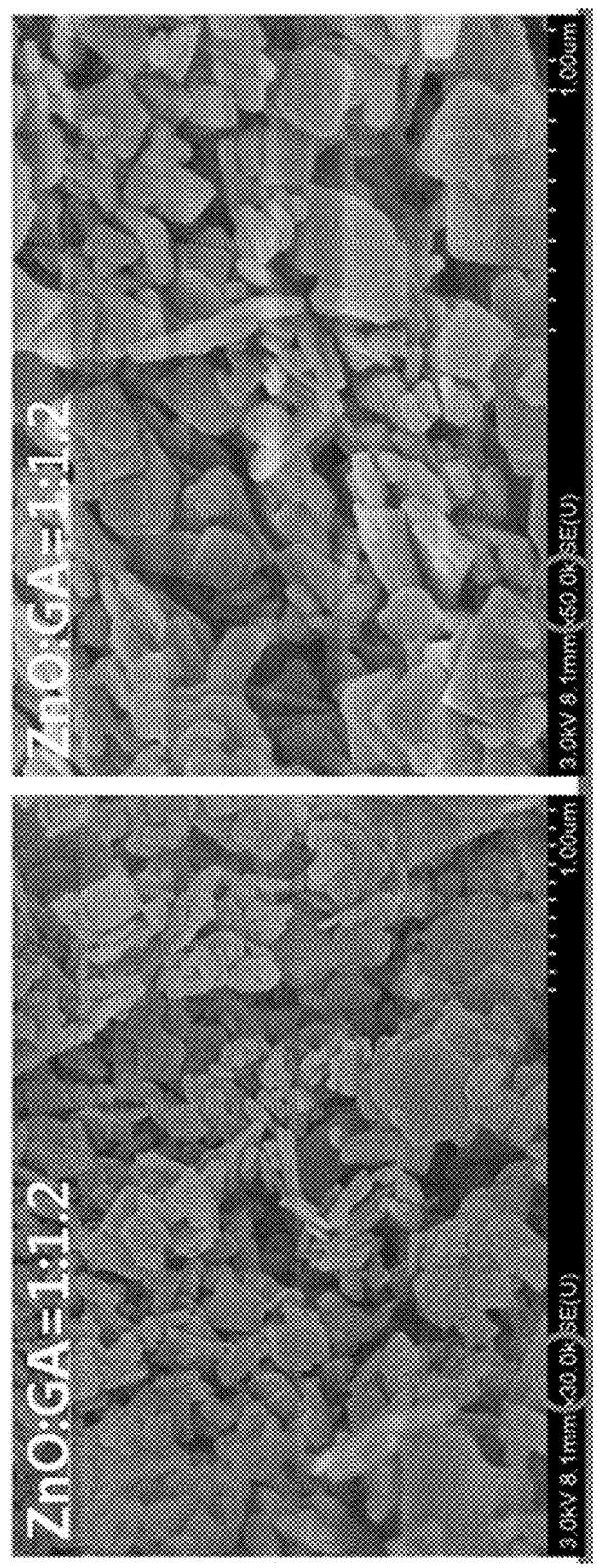
FIGS. 1 and 2 are scanning electron microscope (SEM) images of organic zinc catalysts obtained from Example 1 and Comparative Example 1, respectively.

Hereinafter, preferable Examples of the present invention will be provided for better understanding of the present invention. However, the following Examples are provided only for illustration of the present invention, and should not be construed as limiting the present invention by the examples.

Example 1: Manufacture of Organic Zinc Catalyst (Molar Ratio of ZnO and Glutaric Acid=1:1.2)

7.93 g (0.06 mol) of a glutaric acid and 0.1 mL of acetic acid were added to 100 mL toluene in a 250 mL size round bottom flask, and dispersed under reflux. Then, the mixture was heated at a temperature of 55° C. for 30 minutes, and 4.1 g (0.05 mol) of ZnO was added to 50 mL of toluene, and dispersed. The reaction was performed by firstly adding 25 vol % of the ZnO dispersion liquid to the glutaric acid dispersion liquid, then after 1 hour, adding another 25 vol % out of 75 vol % of the ZnO dispersion liquid to the glutaric acid dispersion liquid, and after 1 hour, adding the third 25 vol % of the ZnO dispersion liquid to the glutaric acid dispersion liquid. Next, after 1 hour, the other 25 vol % of the ZnO dispersion liquid was lastly added to the glutaric acid dispersion liquid. The mixed solution was heated at 110° C. for 2 hours. A white solid was produced, filtered and washed with acetone/ethanol, and dried in a vacuum oven at 130° C.

According to the above-described method, the organic zinc catalyst of Example 1 was manufactured. A scanning electron microscope (SEM) image of the organic zinc catalyst of Example 1 was shown in FIG. 1. It was confirmed from the SEM analysis that the organic zinc catalyst of Example 1 had an average particle size of about 0.5 μm and a particle size standard deviation of about 0.13 μm.

Example 2: Manufacture of Organic Zinc Catalyst (Molar Ratio of ZnO and Glutaric Acid=1:1.5)

9.91 g (0.075 mol) of a glutaric acid and 0.1 mL of acetic acid were added to 100 mL toluene in a 250 mL size round bottom flask, and dispersed under reflux. Then, the mixture was heated at a temperature of 55° C. for 30 minutes, and 4.1 g (0.05 mol) of ZnO was added to 50 mL of toluene, and dispersed. The reaction was performed by firstly adding 25 vol % of the ZnO dispersion liquid to the glutaric acid dispersion liquid, then after 1 hour, adding another 25 vol % out of 75 vol % of the ZnO dispersion liquid to the glutaric acid dispersion liquid, and after 1 hour, adding the third 25 vol % of the ZnO dispersion liquid to the glutaric acid dispersion liquid. Next, after 1 hour, the other 25 vol % of the ZnO dispersion liquid was lastly added to the glutaric acid dispersion liquid. The mixed solution was heated at 110° C. for 2 hours. A white solid was produced, filtered and washed with acetone/ethanol, and dried in a vacuum oven at 130° C.

According to the above-described method, the organic zinc catalyst of Example 2 was manufactured. The organic zinc catalyst of Example 2 was confirmed by SEM analysis. As a result, it was confirmed that the organic zinc catalyst of Example 2 had an average particle size of about 0.8 μm and a particle size standard deviation of about 0.19 μm.

Example 3: Manufacture of Organic Zinc Catalyst (Molar Ratio of ZnO and Glutaric Acid=1:1)

6.61 g (0.05 mol) of a glutaric acid and 0.1 mL of acetic acid were added to 100 mL toluene in a 250 mL size round bottom flask, and dispersed under reflux. Then, the mixture was heated at a temperature of 55° C. for 30 minutes, and 4.1 g (0.05 mol) of ZnO was added to 50 mL of toluene, and dispersed. The reaction was performed by firstly adding 25 vol % of the ZnO dispersion liquid to the glutaric acid dispersion liquid, then after 1 hour, adding another 25 vol % out of 75 vol % of the ZnO dispersion liquid to the glutaric acid dispersion liquid, and after 1 hour, adding the third 25 vol % of the ZnO dispersion liquid to the glutaric acid dispersion liquid. Next, after 1 hour, the other 25 vol % of the ZnO dispersion liquid was lastly added to the glutaric acid dispersion liquid. The mixed solution was heated at 110° C. for 2 hours. A white solid was produced, filtered and washed with acetone/ethanol, and dried in a vacuum oven at 130° C.

According to the above-described method, the organic zinc catalyst of Example 3 was manufactured. The organic zinc catalyst of Example 3 was confirmed by SEM analysis. As a result, it was confirmed that the organic zinc catalyst of Example 3 had an average particle size of about 0.6 μm and a particle size standard deviation of about 0.18 μm.

Example 4: Manufacture of Organic Zinc Catalyst (Molar Ratio of Zinc Nitrate ($Zn(NO_3)_2$) and Glutaric Acid=1:1.2)

The organic zinc catalyst of Example 4 was manufactured by the same method as Example 1 except for using 11.36 g (0.06 mol) of $Zn(NO_3)_2$ instead of using ZnO, as the zinc precursor. The organic zinc catalyst of Example 4 was confirmed by SEM analysis. As a result, it was confirmed that the organic zinc catalyst of Example 4 had an average particle size of about 0.8 μm and a particle size standard deviation of about 0.20 μm.

Comparative Example 1: Manufacture of Organic Zinc Catalyst (Molar Ratio of ZnO and Glutaric Acid=1:1)

6.61 g (0.05 mol) of a glutaric acid, 4.1 g (0.05 mol) of ZnO and 0.1 mL of acetic acid were added to 150 mL toluene in a 250 mL size round bottom flask, and dispersed under reflux. Next, the mixed solution was heated at 55° C. for 3 hours, and further heated at 110° C. for 4 hours. A white solid was produced, filtered and washed with acetone/ethanol, and dried in a vacuum oven at 130° C.

Figure 2:
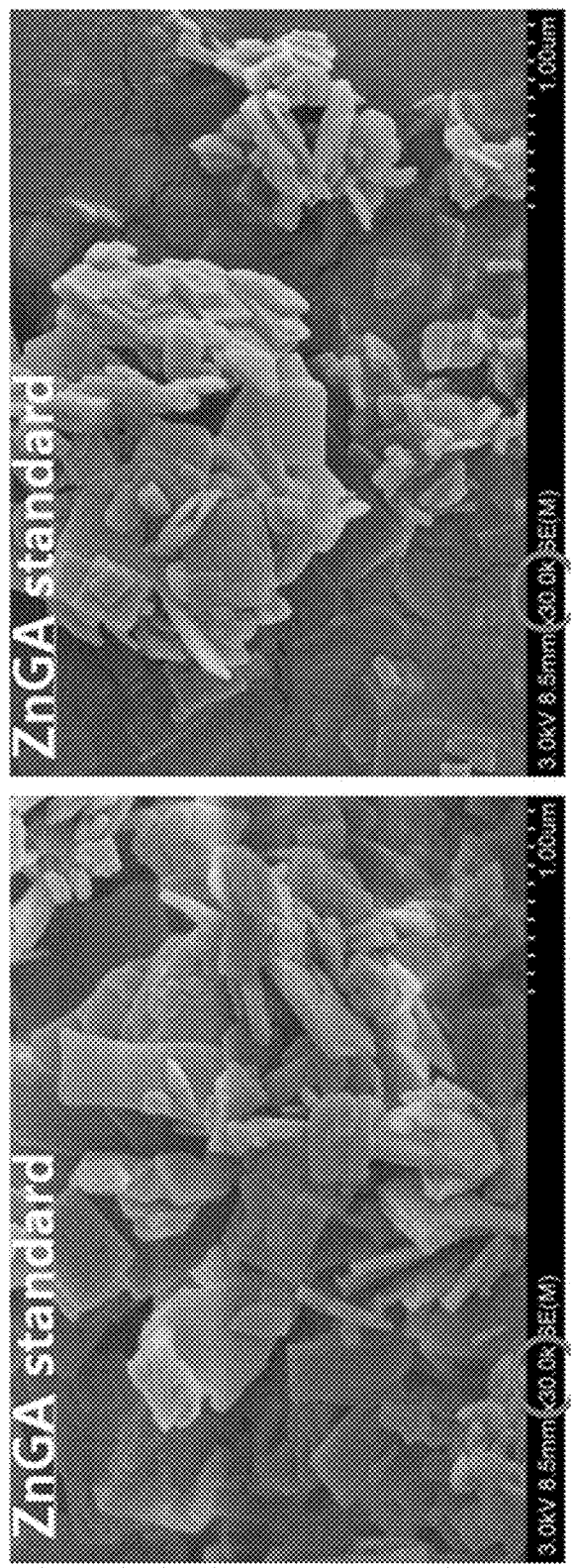

According to the above-described method, the organic zinc catalyst of Comparative Example 1 was manufactured. A scanning electron microscope (SEM) image of the organic zinc catalyst of Comparative Example 1 was shown in FIG. 2. It was confirmed from the SEM analysis that the organic zinc catalyst of Comparative Example 1 had a particle size of about 1 to 2 μm and a particle size standard deviation of about 0.4 μm or more.

Comparative Example 2: Manufacture of Organic Zinc Catalyst (Molar Ratio of ZnO and Glutaric Acid=1:1.2)

7.93 g (0.06 mol) of a glutaric acid and 0.1 mL of acetic acid were added to 100 mL toluene in a 250 mL size round bottom flask, and dispersed under reflux. Then, the mixture was heated at a temperature of 55° C. for 30 minutes, and 4.1 g (0.05 mol) of ZnO was added to 50 mL of toluene, and dispersed. The reaction was performed by firstly adding 25 vol % of the glutaric acid dispersion liquid to the ZnO dispersion liquid, then after 1 hour, adding another 25 vol % out of 75 vol % of the glutaric acid dispersion liquid to the ZnO dispersion liquid, and after 1 hour, adding the third 25 vol % of the glutaric acid dispersion liquid to the ZnO dispersion liquid. Next, after 1 hour, the other 25 vol % of glutaric acid dispersion liquid was lastly added to the ZnO dispersion liquid. The mixed solution was heated at 110° C. for 2 hours. A white solid was produced, filtered and washed with acetone/ethanol, and dried in a vacuum oven at 130° C.

According to the above-described method, the organic zinc catalyst of Comparative Example 2 was manufactured. The organic zinc catalyst of Comparative Example 2 was confirmed by SEM analysis. As a result, it was confirmed that the organic zinc catalyst of Comparative Example 2 had an average particle size of about 1.7 μm and a particle size standard deviation of about 0.43 μm or more.

Polymerization Example

Polyethylene carbonates were polymerized and manufactured by performing the following method and using the catalysts of Examples 1 to 4 and Comparative Examples 1 and 2.

First, 0.4 g of each catalyst and 8.52 g of dichloromethane (methylene chloride) were added to a high-pressure reactor in a glove box, and 8.9 g of ethylene oxide was added. Then, the mixture was pressed in the reactor by a pressure of 30 bar using carbon dioxide. The polymerization reaction was performed at 70° C. for 3 hours. After the reaction was completed, unreacted carbon dioxide and ethylene oxide were removed together with dichloromethane which is a solvent. In order to measure an amount of the manufactured polyethylene carbonate, the remaining solid was completely dried and quantified. Each activity and yield of the catalysts according to the polymerization results were shown in Table 1 below.

TABLE 1

|  | Molar ratio of ZnO:Glutaric acid | Yield (g) | Activity of catalyst (g-polymer/g-catalyst) |
| --- | --- | --- | --- |
| Example 1 | 1:1.2 | 20.9 | 52.3 |
| Example 2 | 1:1.5 | 16.5 | 36.2 |
| Example 3 | 1:1 | 20.1 | 50.3 |
| Example 4[a] | 1:1.2 | 14.3 | 35.8 |
| Comparative Example 1 | 1:1 | 11.9 | 29.8 |
| Comparative Example 2[b] | 1:1.2 | 10.2 | 25.5 |

[a] Example 4: $Zn(NO_3)_2$ was used instead of using ZnO;
[b] Comparative Example 2: Glutaric acid was separately added to ZnO dispersion liquid.

Referring to Table 1 above, it was confirmed that the catalysts of Examples 1 to 4 had more excellent activity than that of Comparative Examples 1 and 2. In addition, from the catalysts of Examples 1 to 4, the polyethylene carbonate could be manufactured at an excellent yield.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A manufacturing method of an organic zinc catalyst comprising:
    forming a zinc dicarboxylate-based catalyst by reacting a zinc precursor with C3-C20 dicarboxylic acid,
    wherein the reaction step is performed under a condition in which the number of moles of the dicarboxylic acid is more than that of the zinc precursor in a reaction system, throughout the entire reaction steps, and
    wherein the reaction step is performed in a liquid medium, and is performed by separately adding a solution or a dispersion liquid containing the zinc precursor to a solution or a dispersion liquid containing the dicarboxylic acid two or more times.

2. The manufacturing method of claim 1, wherein:
    the dicarboxylic acid has a molar ratio of 1.05 to 1.5 relative to 1 mol of the zinc precursor.

3. The manufacturing method of claim 1, wherein:
    the zinc precursor includes a zinc compound selected from the group consisting of zinc oxide, zinc sulfate ($ZnSO_4$), zinc chlorate ($Zn(ClO_3)_2$), zinc nitrate ($Zn(NO_3)_2$), zinc acetate ($Zn(OAc)_2$, and zinc hydroxide.

4. The manufacturing method of claim 1, wherein:
    the C3-C20 dicarboxylic acid includes an aliphatic dicarboxylic acid selected from the group consisting of a malonic acid, a glutaric acid, a succinic acid, and an adipic acid, or an aromatic dicarboxylic acid selected from the group consisting of a terephthalic acid, an isophthalic acid, a homophthalic acid, and a phenylglutaric acid.

5. The manufacturing method of claim 1, wherein:
    the reaction step is performed by adding the solution or the dispersion liquid containing the zinc precursor to the solution or the dispersion liquid containing the dicarboxylic acid at an equal time interval with an amount at which the total used amount of the zinc precursor is divided into two to ten parts.

6. The manufacturing method of claim 1, wherein:
the reaction step is performed by dropping the solution or the dispersion liquid containing the zinc precursor in droplet forms onto the solution or the dispersion liquid containing the dicarboxylic acid.

7. The manufacturing method of claim 1, wherein:
the liquid medium includes at least one solvent selected from the group consisting of toluene, hexane, DMF, ethanol and water.

8. The manufacturing method of claim 1, wherein:
the organic zinc catalyst in a particle shape having an average particle size of 0.8 μm or less and a particle size standard deviation of 0.2 μm or less is manufactured.

9. The manufacturing method of claim 1, wherein:
the organic zinc catalyst having a surface area of 1.8 $m^2/g$ or more is manufactured.

10. The manufacturing method of claim 1, wherein:
the reaction step is performed at a temperature of 50 to 130° C. for 1 to 10 hours.

11. A manufacturing method of a polyalkylene carbonate resin comprising:
polymerizing an epoxide and a monomer including carbon dioxide in the presence of the organic zinc catalyst manufactured by the method of claim 1.

12. The manufacturing method of claim 11, wherein:
the manufacturing method is performed in an organic solvent by solution polymerization.

* * * * *